(12) United States Patent
Kim et al.

(10) Patent No.: US 10,835,461 B2
(45) Date of Patent: Nov. 17, 2020

(54) BIO-ACTIVE MATERIAL COMPOSITE, PREPARING METHOD THEREOF AND COSMETIC COMPOSITION CONTAINING THE SAME

(71) Applicant: Bae Yong Kim, Seoul (KR)

(72) Inventors: Bae Yong Kim, Seoul (KR); Jai Soon Myung, Chuncheon-si (KR); Ji Yeon Roh, Seongnam-si (KR)

(73) Assignee: Bae Yong Kim, Seoul (KR)

( * ) Notice: Subject to any disclaimer, the term of this patent is extended or adjusted under 35 U.S.C. 154(b) by 0 days.

(21) Appl. No.: 15/780,041

(22) PCT Filed: Nov. 22, 2016

(86) PCT No.: PCT/KR2016/013470
§ 371 (c)(1),
(2) Date: May 30, 2018

(87) PCT Pub. No.: WO2017/095055
PCT Pub. Date: Jun. 8, 2017

(65) Prior Publication Data
US 2018/0369084 A1  Dec. 27, 2018

(30) Foreign Application Priority Data

Dec. 1, 2015 (KR) .................. 10-2015-0170124

(51) Int. Cl.
| | | |
|---|---|---|
| *A61K 8/19* | (2006.01) | |
| *A61Q 19/02* | (2006.01) | |
| *A61Q 19/08* | (2006.01) | |
| *A61K 8/49* | (2006.01) | |
| *A61K 8/368* | (2006.01) | |
| *A61K 8/36* | (2006.01) | |
| *A61K 8/02* | (2006.01) | |
| *A61K 8/34* | (2006.01) | |
| *A61K 8/365* | (2006.01) | |
| *A61K 8/64* | (2006.01) | |
| *A61K 8/67* | (2006.01) | |

(52) U.S. Cl.
CPC ............. *A61K 8/19* (2013.01); *A61K 8/0254* (2013.01); *A61K 8/347* (2013.01); *A61K 8/361* (2013.01); *A61K 8/365* (2013.01); *A61K 8/368* (2013.01); *A61K 8/498* (2013.01); *A61K 8/4953* (2013.01); *A61K 8/4986* (2013.01); *A61K 8/64* (2013.01); *A61K 8/671* (2013.01); *A61K 8/676* (2013.01); *A61Q 19/02* (2013.01); *A61Q 19/08* (2013.01); *A61K 2800/522* (2013.01); *A61K 2800/592* (2013.01); *A61K 2800/74* (2013.01)

(58) Field of Classification Search
None
See application file for complete search history.

(56) References Cited

U.S. PATENT DOCUMENTS

2009/0220698 A1* 9/2009 Yadav .................... B82Y 30/00
427/383.5

FOREIGN PATENT DOCUMENTS

| CN | 1417211 | | 5/2003 |
|---|---|---|---|
| CN | 102268252 | * | 1/2014 |
| CN | 104277243 | | 1/2015 |
| KR | 20070054191 | | 5/2007 |
| KR | 20070079166 | | 8/2007 |
| KR | 101511253 | | 4/2015 |

OTHER PUBLICATIONS

Xiang et al. (Adv. Funct. Mater. 2011, 21:4388-4396).*
Liang et al. (Dalton Trans., 2014, 43:10355-10364).*
English Translation of CN102268252 (2014).*
International Search Report—PCT/KR2016/013470 dated Mar. 7, 2017.
Mellado-Vazquez, et al., Sol-Gel Synthesis and Antioxidant Properties of Yttrium Oxide Nanocrystallites Incorporating P-123, Materials, 2014, pp. 6768-6778.
Mohammad, et al., Antioxidant Properties of Some Nanoparticle May Enhance Wound Healing in T2DM Patient, Digest Journal of Nanomaterials and Biostructures, 2008, pp. 159-162.
Ranjbar, et al., Yttria Nanoparticles Prepared from Salicylic Acid-Y(III) Nanocomposite as a New Precursor, American Chemical Science Journal, 2013, pp. 1-10.
Schubert, et al., Cerium and yttrium oxide nanoparticles are neuroprotective, Biochemical and Biophysical Research Communications, 2006, pp. 86-91.
Lee, et al., A layered polymorph of rare earth hydroxides, Chem. Commun., 2013, pp. 6051-6053.
Sato, et al., Changes in crystal phases and morphologies of rare earth hydroxide nitrates with ionic radius, Journal of the Ceramic Society of Japan, 2017, pp. 737-741.

* cited by examiner

*Primary Examiner* — Bong-Sook Baek
(74) *Attorney, Agent, or Firm* — Cantor Colburn LLP

(57) ABSTRACT

Provided is a composite containing bio-active material stably combined with a rare-earth hydroxide compound having a layered structure. The bio-active materials in the composite are preserved in terms of long-term stability at high temperature of 50° C. or above and the composite maintained in the neutral pH condition to minimize side effects like latent toxicity, irritations, etc. Further, the present invention is useful for a skin-whitening, anti-wrinkle, or anti-aging cosmetic composition containing the composite.

14 Claims, 8 Drawing Sheets

BIO-ACTIVE MATERIAL COMPOSITE, PREPARING METHOD THEREOF AND COSMETIC COMPOSITION CONTAINING THE SAME

TECHNICAL FIELD

The present invention relates to a bio-active material composite, preparing method thereof and cosmetic composition containing the same, more specially, to a composite of a bio-active material combined with a rare-earth hydroxide compound, a preparation method for the bio-active material composite, and a skin-whitening, skin-brightening, anti-wrinkle, or anti-aging cosmetic composition containing the bio-active material composite.

BACKGROUND ART

A bio-active material is a compound having a great effect on the functions and physiological functions of living bodies in a small quantity and includes vitamins, hydroxy acids, unsaturated fatty acids, hormones, enzymes, neurotransmitters, etc.

Vitamins, including vitamin A (retinol), vitamin C (ascorbic acid), vitamin E (tocopherol), and their derivatives, play a very important role in skin whitening, prevention of pigmentation, promotion of collagenesis, UV protection, prevention of dry and scaly skin, reduction of wrinkle, and skin moisturization. With these virtues, the vitamins are drawing attention as an ingredient of functional cosmetics. Nevertheless, vitamins have lots of limitations in practical applications, as they are problematic in terms of stability, irritations, toxicity, or dispersability and inherently unstable, namely, vulnerable to heat, light, oxygen, etc.

Besides, bio-active materials, including hydroxy acids such as salicylic acid, unsaturated fatty acids, and glutathione (GLT), are known to have functions of anti-oxidation, acne treatment, skin whitening, removal of dead skin and age spots, skin moisturization, anti-wrinkle, etc. Like vitamins, these bio-active materials are vulnerable to oxidation by light and heat to undergo a change in color and odor and hence very limited in their practical applications.

For this reason, many studies have been made on the method of stabilizing various bio-active materials including vitamins. The stabilization methods for vitamin C, for example, involve using emulsions, liquid crystal multilayers, or liposomes, encapsulation with water-soluble polymers and polysaccharides, adding an antioxidant, preventing oxidation using zinc sulfate and L-tyrosine, and so forth. In particular, KR No. 2007-0079166 discloses a method of capturing a high amount of vitamin C or its derivative in the inner phase of a water-in-oil type formulation for stabilization to prevent the decomposition of vitamin C or its derivative from the external environments like moisture, temperature, air, etc. It is, however, known that these methods are not effective in enhancing the stability of bio-active materials. Hence, there is a demand for development of methods to effectively stabilize the highly unstable bio-active materials.

In association with the studies on the metal hydroxides, there is a method for stabilizing a bio-active material with a layered metal hydroxide compound, preferably a double-layered metal hydroxide compound. But, the method is reported to be problematic, such as having a low content of the bio-active material per unit weight (25 wt % of vitamin C) or releasing or breaking the stabilized bio-active material upon exposure to water or heat according to a research on the release behaviors of vitamin C inserted into the double-layered metal hydroxide compound.

The transition metals can have various oxidation numbers and participate in chemical reactions, as the d orbitals filled with the outermost electrons are exposed to the external environments. For this reason, a highly reactive transition metal, if used as an interlayer central metal ion, can be released to cause latent toxicity. Unlike the transition metals, rare-earth metals have low reactivity as the f orbitals filled with the outermost electrons are located inside the shell. Further, they are mostly stable with an oxidation number of +3 and thus suitable as an interlayer central metal for stabilizing bioactive materials.

The rare-earth elements are metallic elements dispersed in tiny quantities in the earth's crust and comprised of seventeen elements, that is, fifteen lanthanides with atomic numbers 57 through 71 (La, Ce, Pr, Nd, Pm, Sm, Eu, Gd, Tb, Dy, Ho, Er, Tm, Yb, and Lu), plus two elements of Sc (scandium) and Y (yttrium) in the Group 3A of the periodic table. The rare-earth elements may be present in the form of salts having an ionic bond with a counter anion (for example, sulfates, nitrates, carbonates, acetates, phosphates, chlorides, etc.) or hydroxides including oxides.

Among those, the oxides containing the rare-earth elements have reported to show an antioxidant function that eliminates reactive oxygen species (ROS) (*Biochem. Biophys. Res. Commun.*, 2006, 342, 86-91; *Materials*, 2014, 7, 6768-6778; *Dig. J. Nanomater. Bios.*, 2008, 3, 159-162).

In an attempt to make a study on the method for effectively stabilizing various bio-active materials, including vitamins, the inventors of the present invention have found out the fact that a rare-earth hydroxide compound having a layered structure can be used as a host material to effectively form a composite stably combined with various bio-active materials that are vulnerable to oxidation by light and heat and ready to change in color and odor, which composite has a high content of the bio-active material per unit weight and secures high long-term stability at high temperature of 50° C. or above, thereby completing the present invention.

DISCLOSURE OF INVENTION

It is an object of the present invention to provide a stabilized bio-active material composite.

It is another object of the present invention to provide a preparation method for the composite.

It is still another object of the present invention to provide a skin-whitening, skin-brightening, anti-wrinkle or anti-aging cosmetic composition containing the composite.

To achieve the objects of the present invention, there is provided a composite containing a bio-active material combined with a rare-earth hydroxide compound.

More preferably, the composite is represented by the following chemical formula 1:

$$[RE(OH)_{3-x} \cdot yH_2O] \cdot [A^{n-}]_{x/n} \cdot [B]_z \quad \text{[Chemical Formula 1]}$$

In the chemical formula 1, RE is at least one or more rare-earth element selected from the group consisting of Y, Sc, La, Ce, Pr, Nd, Pm, Sm, Eu, Gd, Tb, Dy, Ho, Er, Tm, Yb, and Lu; A is an anion selected from the group consisting of $F^-$, $Cl^-$, $ClO_3^-$, $ClO_4^-$, $Br^-$, $BrO_3^-$, $I^-$, $IO_3^-$, $IO_4^-$, $I_3^-$, $OH^-$, $CO_3^{2-}$, $HCO_3^-$, $NO_3^-$, $SO_4^{2-}$, $PO_4^{3-}$, $HPO_4^{2-}$, and $H_2PO_4^-$; y is greater than zero, that is, $0<y$; n is the charge number of the anion; x is greater than 0 and less than 3, that is, $0<x<3$; B is a bioactive compound; and z is greater than zero, that is, $0<z$.

Preferably, the bio-active material may be combined with the rare-earth hydroxide compound, where the bio-active material is at least one or more selected from the group consisting of vitamin A, vitamin C, salicylic acid, kojic acid, alpha-lipoic acid, ellagic acid, resveratrol, caffeine, docosahexaenoic acid, eicosapentaenoic acid, linoleic acid, and glutathione.

Furthermore, the present invention provides a skin-whitening, anti-wrinkle, or anti-aging cosmetic composition including a composite of a bio-active material with a rare-earth hydroxide compound.

Effects of the Invention

The present invention provides a composite using a rare-earth hydroxide compound for stabilizing a bio-active material susceptible to oxidation by light and heat and ready to change in color and odor, thereby enabling the use of the bio-active material in a variety of applications and maintaining the neutral pH condition to minimize side effects like latent toxicity, irritations, etc.

Further, the preparation method for a composite according to the present invention offers economic benefits in view of the preparation process, provides a very high content of the bio-active material per unit weight relative to the conventional techniques for stabilizing bio-active materials, and realizes an effective stabilization of various bio-active materials through formation of a composite with a rare-earth hydroxide compound, thereby leading to the high and long-term stability of the bio-active materials even at high temperatures of 50° C. or above.

Accordingly, the composite containing a bio-active material combined with a rare-earth hydroxide compound according to the present invention secures the efficacies of the bio-active material stably for a long time and maintains the neutral pH condition to minimize side effects, such as latent toxicity, irritations, etc. Hence, the composite of the present invention is also useful for a skin-whitening, anti-wrinkle, or anti-aging cosmetic composition.

BRIEF DESCRIPTIONS OF DRAWINGS

BEST MODES FOR CARRYING OUT THE INVENTION

Hereinafter, the present invention will be described in detail.

The present invention provides a composite containing a bio-active material combined with a rare-earth hydroxide compound.

In the composite of the present invention, the composite is preferably represented by the following chemical formula 1:

$$[RE(OH)_{3-x} \cdot yH_2O] \cdot [A^{n-}]_{x/n} \cdot [B]_z \qquad \text{[Chemical Formula 1]}$$

In the chemical formula 1, RE is at least one or more rare-earth element selected from the group consisting of Y, Sc, La, Ce, Pr, Nd, Pm, Sm, Eu, Gd, Tb, Dy, Ho, Er, Tm, Yb, and Lu; A is an anion selected from the group consisting of $F^-$, $Cl^-$, $ClO_3^-$, $ClO_4^-$, $Br^-$, $BrO_3^-$, $I^-$, $IO_3^-$, $IO_4^-$, $I_3^-$, $OH^-$, $CO_3^{2-}$, $HCO_3^-$, $NO_3^-$, $SO_4^{2-}$, $PO_4^{3-}$, $HPO_4^{2-}$, and $H_2PO_4^-$; y is greater than zero, that is, $0<y$; n is the charge number of the anion; x is greater than 0 and less than 3, that is, $0<x<3$; B is a bioactive compound; and z is greater than zero, that is, $0<z$.

Preferably, the bio-active material may be combined with the rare-earth compound, where the bio-active material is at least one or more selected from the group consisting of vitamin A, vitamin C, salicylic acid, kojic acid, alpha-lipoic acid, ellagic acid, resveratrol, caffeine, docosahexaenoic acid, eicosapentaenoic acid, linoleic acid and glutathione.

In the preferred embodiment of the present invention, specific examples of the rare-earth (RE) hydroxide compound may include, but are not limited to, Pr, Nd, Sm, Eu, Gd, Tb, Dy, Y, Ce, Y/Ce, or Gd/Eu [FIGS. 1 to 5].

Figure 6:
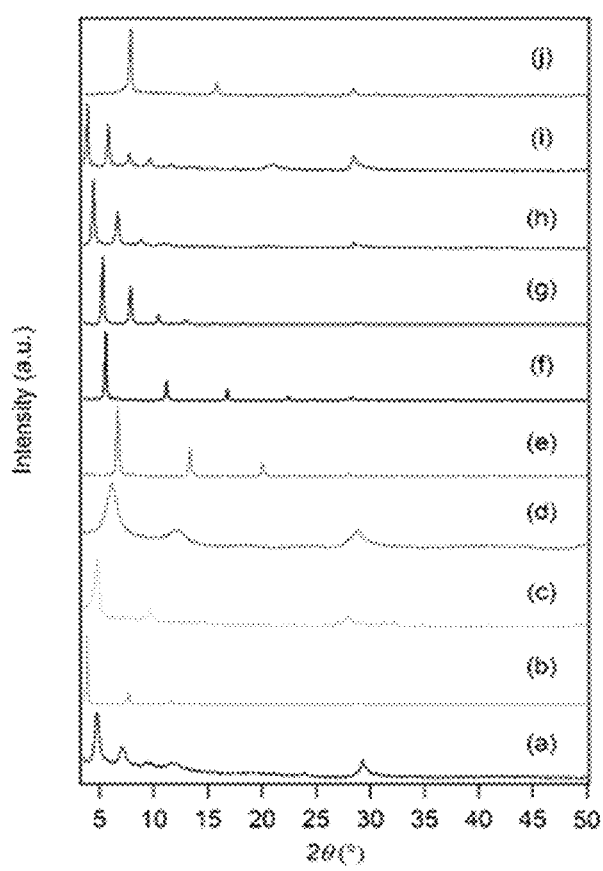
FIG. 6 is the X-ray diffraction diagram of (a) vitamin A, (b) salicylic acid, (c) kojic acid, (d) alpha-lipoic acid, (e) ellagic acid, (f) resveratrol, (g) docosahexaenoic acid, (h) eicosapentaenoic acid, (i) linoleic acid, and (j) glutathione combined with the yttrium hydroxide compound (YHC) according to the present invention.

More preferably, the present invention can synthesize a variety of composites containing bio-active materials combined with yttrium hydroxide [FIG. 6]. The composites are stably maintained without significant change in terms of color [FIGS. 7 and 9] and bio-active material content [FIGS. 8 and 10, and Table 4] and constantly preserved in the neutral pH condition [Tables 2 and 3] for four weeks at 50° C. in an airtight container. This is supported by the fact that the bio-active materials are stably combined with the rare-earth hydroxide compound.

The rare-earth hydroxide compound may be easily dispersed in an aqueous medium to form a stable colloidal suspension. More preferably, the rare-earth hydroxide compound may have a layered structure.

Accordingly, the composite of the present invention contains a bio-active material combined with the rare-earth hydroxide compound through method, including substitution, interlayer insertion, adsorption, or encapsulation alone or in combination, so that the bio-active material can be maintained stably even under high-temperature conditions for a long time.

The present invention also provides a method for preparing a composite containing a bio-active material combined with a rare-earth hydroxide compound that includes the steps of reacting an aqueous solution of rare-earth salt with a base solution to obtain a rare-earth hydroxide compound and mixing the rare-earth hydroxide compound with a bio-active material to cause a reaction.

In the preparation method of the present invention, the rare-earth salt used in the step of obtaining a rare-earth hydroxide compound may be a chloride, nitrate, or sulfate containing a rare-earth element. Preferably, the rare-earth salt is a chloride or nitrate of a rare-earth element.

The base solution used in the step of obtaining a rare-earth hydroxide compound is selected from the group consisting of NaOH, KOH, RbOH, CsOH and $NH_4OH$. Preferably, the base solution is a solution of NaOH or KOH.

The step of obtaining a rare-earth hydroxide compound may be performed by adding a base solution dropwise to an aqueous solution of rare-earth salt and then causing a reaction at 0 to 200° C. for 0 to 24 hours, preferably by heating at 50 to 100° C. for 12 to 24 hours.

The step of obtaining a rare-earth hydroxide compound may further include a step of washing and drying the product after heating.

In the preparation method of the present invention, the step of mixing and reacting the rare-earth hydroxide compound with a bio-active material may be performed by mixing the rare-earth hydroxide compound with a solution of a bio-active material to cause a reaction at 0 to 100° C. for 1 to 48 hours, preferably 50 to 100° C. for 24 to 48 hours.

In the step of mixing and reacting the rare-earth hydroxide compound with a bioactive compound, a bio-active material or a solution containing a salt of the bio-active material is used; or an anionic bio-active material is obtained by reacting a bio-active material with a base solution before a reaction with the rare-earth hydroxide compound, so that a composite is formed between the bio-active material and the rare-earth hydroxide compound through an electrostatic interaction. In other words, there may occur a formation of composite that involves substitution of the bio-active material with an anion in the rare-earth hydroxide compound according to the chemical formula 1; interlayer insertion of the bio-active material into the interlayer structure of the rare-earth hydroxide compound; adsorption of the bio-active material on the surface of the interlayer structure of the rare-earth hydroxide compound; a combination of interlayer insertion and adsorption; or a combination of substitution, interlayer insertion, adsorption, and encapsulation.

According to the embodiments of the present invention, the composite of bio-active material formed by using a rare-earth hydroxide compound is stable even at high temperatures of 50° C. or above for a long time and has a high content of the bio-active material per unit weight. This is supported by the formation of composite that involves: the insertion of the bio-active material into the interlayer structure of the rare-earth hydroxide compound; the adsorption of the bio-active material on the surface of the interlayer rare-earth hydroxide compound; a combination of insertion and adsorption; or a combination of insertion adsorption and encapsulation.

The step of mixing and reacting the rare-earth hydroxide compound with a bio-active material may further include a step of washing and drying the composite product.

Furthermore, the present invention provides a cosmetic composition containing a composite of a bio-active material combined with a rare-earth hydroxide compound which the cosmetic composition is useful for a skin-whitening, anti-wrinkle, or anti-aging.

When applied to a cosmetic, the composite of the present invention can effectively stabilize the beneficial bioactive compound, thereby preserving the performances of the bio-active material for a long time and maintaining the neutral pH condition to minimize side effects like latent toxicity, irritations, etc. The bio-active material is vitamin A, vitamin C, salicylic acid, kojic acid, alpha-lipoic acid, ellagic acid, resveratrol, caffeine, docosahexaenoic acid, eicosapentaenoic acid, linoleic acid and glutathione with skin-whitening, skin-brightening, anti-wrinkle or anti-aging functions.

In this regard, the cosmetic composition of the present invention contains the composite as an active ingredient in an amount of 0.1 to 50 wt %, preferably 0.5 to 10 wt %. The content of the active ingredient may be determined appropriately depending on the use purpose of the active ingredient.

Further, the cosmetic composition of the present invention may further include ingredients ordinarily available in the cosmetic compositions in additives; for example, typical carriers and adjuvants like antioxidants, stabilizers, solubilizers, vitamins, pigments, fragrances, etc.

Further, the cosmetic composition of the present invention may further include at least one or more known substance having skin-whitening, skin-brightening, anti-wrinkle or anti-aging functions.

The cosmetic composition of the present invention may be manufactured into any formulation generally available in the related art; for example, solutions, suspensions, emulsions, pastes, gels, creams, powder, spray, etc.

The component available for the paste, cream, or gel type formulation of the present invention may include animal oils, vegetable oils, wax, paraffin, starch, tragacanth, cellulose derivatives, polyethylene glycol, silicone, bentonite, silica, talc, zinc oxide, etc.

The component available for the powder or spray type formulation of the present invention may include lactose, talc, silica, aluminum hydroxide, calcium silicate, polyamide powder, etc. Particularly, spray as the formulation of the present invention may further include a repellent, such as chlorofluorohydrocarbon, propane/butane or dimethyl ether.

Also, in the case where the formulation of the present invention is a solution or an emulsion, solvents, solubilizers, or emulsifiers; for example, water, ethanol, isopropanol, ethyl carbonate, ethyl acetate, benzyl alcohol, benzyl benzoate, propylene glycol, 1,3-butylglycol oil, glycerol with aliphatic ester, polyethylene glycol, aliphatic ester of sorbitan, etc. can be used.

The suspension type formulation of the present invention may include a liquid-state diluent (e.g., water, ethanol, or propylene glycol), a suspending agent (e.g., ethoxylated isostearyl alcohol, polyoxyethylene sorbitol ester, or polyoxyethylene sorbitan ester), microcrystalline cellulose, aluminum meta-hydroxide, bentonite, agar, tragacanth, etc.

The cosmetic composition of the present invention as described above may be applied to skin toner, lotion, cream, essence, pack, foundation, pigment cosmetics, sunscreen, two-way cakes, face powder, compact, make-up base, skin cover, eye shadow, lipstick, lip gloss, lip picks, eyebrow pencil, etc.

Hereinafter, the present invention will be described in further detail with reference to the following examples.

The embodiments of the present invention are given only for the better understanding of the present invention and not construed to limit the scope of the present invention.

Example 1 Preparation of Rare-Earth Hydroxide Compound

For use in the stabilization of a bio-active material including vitamins, a base solution was added dropwise to an aqueous solution of a rare-earth salt and then a heating process was performed to prepare a variety of rare-earth hydroxide compounds (REHC).

More specifically, a 0.5M $RECl_3.xH_2O$ (where RE is Pr, Nd, Sm, Eu, Gd, Tb, or Dy) solution and a 1.0M KOH solution were mixed together. The resultant colloid was allowed to undergo a reaction at 60° C. for at least 12 hours, collected by centrifugal separation, washed, and dried into a rare-earth hydroxide compound (REHC) in the powder form.

Figure 1:
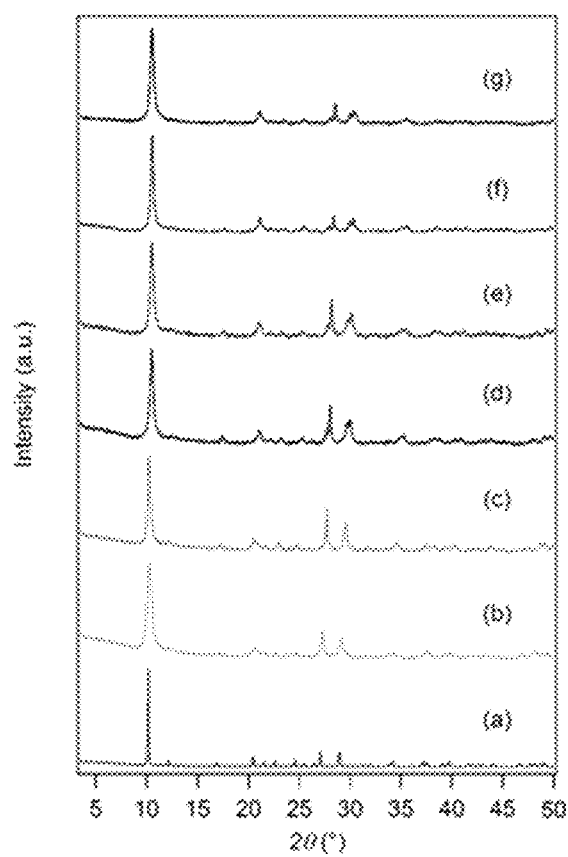
FIG. 1 is the X-ray diffraction (XRD) diagram of various rare-earth hydroxide compounds.

FIG. 1 is the X-ray diffraction diagram of various rare-earth hydroxide compounds of (a) Pr, (b) Nd, (c) Sm, (d) Eu, (e) Gd, (f) Tb, and (g) Dy, showing that the individual rare-earth hydroxide compounds were successfully synthesized.

Example 2 Preparation of Composite (YHC-Vc) of Vitamin C Combined with Rare-Earth Hydroxide Compound The procedures were performed in the same manner as described in the preparation of rare-earth hydroxide compounds in the Example 1 to prepare an yttrium hydroxide compound (YHC). The powder of the yttrium hydroxide compound was added to a solution of vitamin C (ascorbic acid) and allowed to undergo a reaction at 50° C. or above under low pressure for at least 24 hours. The precipitate thus obtained was collected through centrifugal separation, washed, and then dried into the powder of a composite (YHC-Vc) containing vitamin C combined with the yttrium hydroxide compound (YHC).

Figure 2:
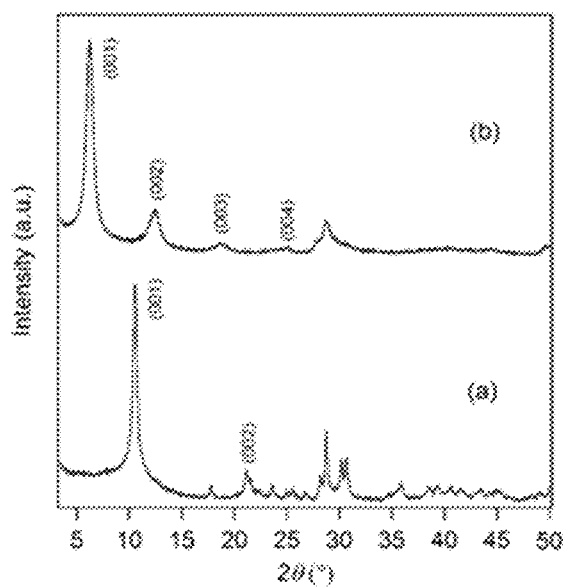
FIG. 2 is the XRD diagram of (a) an yttrium hydroxide compound (YHC); and (b) a composite (YHC-Vc) of vitamin C combined with the yttrium hydroxide compound.

FIG. 2 is the XRD diagram of (a) the yttrium hydroxide compound (YHC); and (b) the composite (YHC-Vc) of vitamin C combined with the yttrium hydroxide compound. The termination of the reaction was identified through the powder X-ray diffraction (PXRD). In other words, the intrinsic diffraction pattern observed in (a) of FIG. 2 shows that a typical yttrium hydroxide compound (YHC) was synthesized. The diffraction pattern of (a) disappears after the reaction with the ascorbic acid, and a series of new diffraction patterns (001) in (b) of FIG. 2 shows up to identify the termination of the reaction.

Figure 3:
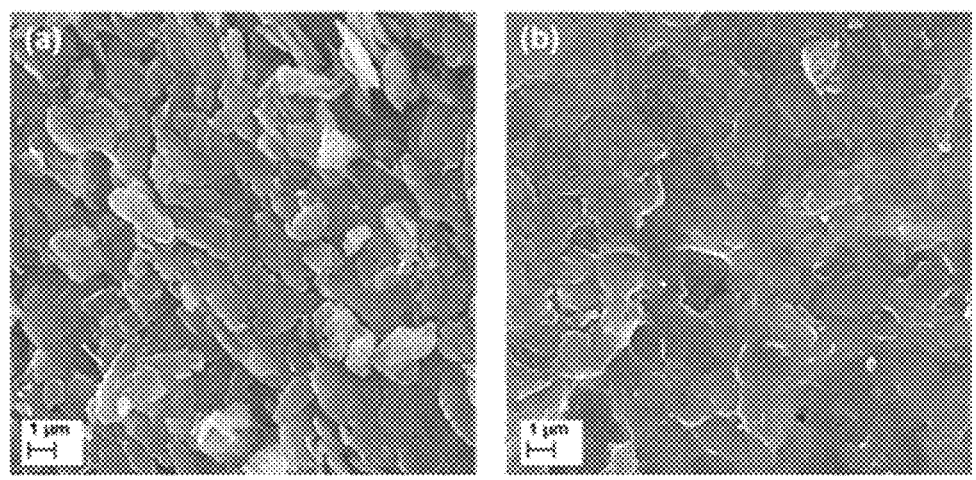
FIG. 3 is the scanning electron microscope (SEM) image microscopic (SEM) image of (a) an yttrium hydroxide compound (YHC); and (b) a composite (YHC-Vc) of vitamin C with the yttrium hydroxide compound.

FIG. 3 is the scanning electron microscope (SEM) image of (a) the yttrium hydroxide compound (YHC); and (b) the composite (YHC-Vc) of vitamin C combined with the yttrium hydroxide compound. It can be seen that the yttrium hydroxide compound (YHC) had a sheet form having a relatively uniform average diameter without a great change in the form even after the reaction with vitamin C.

In addition, the pure vitamin C content of the composite (YHC-Vc) containing vitamin C combined with the yttrium hydroxide compound was determined through a thermogravimetric analysis and a high-performance liquid chromatography (HPLC). The results are presented in Table 1.

TABLE 1

| Pure Vitamin C Content of Composite (YHC-Vc) of Vitamin C combined with Yttrium Hydroxide Compound | | |
|---|---|---|
| Div. | Thermogravimetric analysis | HPLC |
| Pure vitamin C (%) | 30.2 | 30.4 |

According to the results, at least about 30 mg of pure vitamin C was contained in 100 mg of the composite on average.

Example 3 Preparation of Composite (Y/CeHC-Vc) of Vitamin C Combined with Rare-Earth Hydroxide Compound The procedures were performed in the same manner as described in the preparation of rare-earth hydroxide compounds in the Example 1; that is, mixing a 0.5M $RECl_3.xH_2O$ (where RE is Y or Ce) solution and a 1.0M KOH solution together to synthesize an yttrium/cerium hydroxide compound (Y/CeHC). The powder of the yttrium/cerium hydroxide compound was added to a solution of vitamin C (ascorbic acid). Then the procedures were performed in the same manner as described in the Example 2 to obtain a composite (Y/CeHC-Vc) containing vitamin C combined with the yttrium/cerium hydroxide compound.

Figure 4:
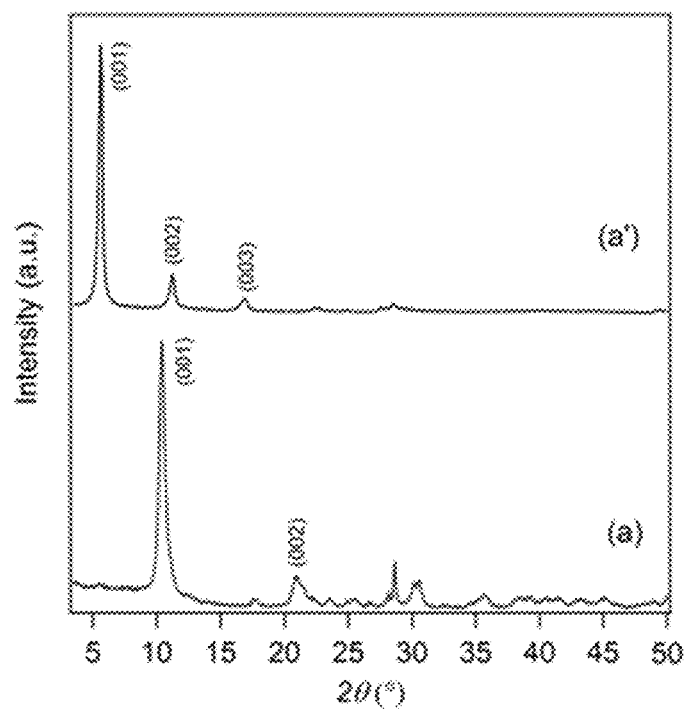
FIG. 4 is the XRD diagram of (a) an yttrium/cerium hydroxide compound (Y/CeHC); and (a') a composite (Y/CeHC-Vc) of vitamin C combined with the yttrium/cerium hydroxide compound.

FIG. 4 is the XRD diagram of (a) the yttrium/cerium hydroxide compound (Y/CeHC); and (a') the composite (Y/CeHC-Vc) of vitamin C combined with the yttrium/cerium hydroxide compound. The intrinsic diffraction pattern observed in (a) shows that the yttrium/cerium hydroxide compound (Y/CeHC) was synthesized. The diffraction pattern of (a) disappears after the reaction with the ascorbic acid, and a series of new diffraction patterns (001) in (a') shows up to identify the termination of the reaction.

Example 4 Preparation of Composite (Gd/EuHC-Vc) of Vitamin C Combined with Rare-Earth Hydroxide Compound The procedures were performed in the same manner as described in the preparation of rare-earth hydroxide compounds in the Example 1; that is, mixing a 0.5M $RECl_3.xH_2O$ (where RE is Gd or Eu) solution and a 1.0M KOH solution together to synthesize a gadolinium/europium hydroxide compound (Gd/EuHC). The powder of the gadolinium/europium hydroxide compound was added to a solution of vitamin C (ascorbic acid). Then the procedures were performed in the same manner as described in the Example 2 to obtain a composite (Gd/EuHC-Vc) containing vitamin C combined with the gadolinium/europium hydroxide compound.

Figure 5:
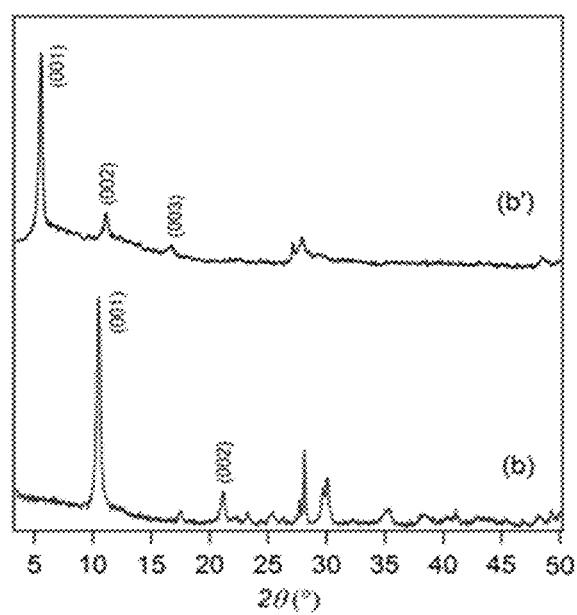
FIG. 5 is the X-ray diffraction (XRD) diagram of (a) a gadolinium/europium hydroxide compound (Gd/EuHC); and (a') a composite (Gd/EuHC-Vc) of vitamin C combined with the gadolinium/europium hydroxide compound.

FIG. 5 is the XRD diagram of (a) the gadolinium/europium hydroxide compound (Gd/EuHC); and (a') the composite (Gd/EuHC-Vc) of vitamin C combined with the gadolinium/europium hydroxide compound. The intrinsic diffraction pattern observed in (a) shows the successful synthesis of the gadolinium/europium hydroxide compound (Gd/EuHC). The diffraction pattern of (a) disappears after the reaction with the ascorbic acid, and a series of new diffraction patterns (001) in (a') shows up to identify the termination of the reaction.

Example 5 Preparation of Composite (YHC-Va) of Vitamin A Combined with Rare-Earth Hydroxide Compound The powder of the yttrium hydroxide compound (YHC) obtained in the Example 1 was added to a solution containing retinoic acid and sodium hydroxide dissolved at an equivalent weight ratio of 1:1 and allowed to undergo a reaction under low pressure for at least 24 hours. The precipitate thus obtained was collected through centrifugal separation, washed with distilled water and then dried into a powder type composite (YHC-Va) of vitamin A combined with the yttrium hydroxide compound (YHC). The X-ray diffraction diagram of FIG. 6(a) shows that the vitamin A is combined with the yttrium hydroxide compound (YHC).

Example 6 Preparation of Composite (YHC-SA) of Salicylic Acid Combined with Rare-Earth Hydroxide Compound The powder of the yttrium hydroxide compound (YHC) obtained in the Example 1 was added to a solution containing salicylic acid and sodium hydroxide dissolved at an equivalent weight ratio of 1:1 and allowed to undergo a reaction at 50° C. or above for at least 24 hours. The precipitate thus obtained was collected through centrifugal separation, washed with distilled water and then dried into a powder type composite (YHC-SA) of salicylic acid combined with the yttrium hydroxide compound (YHC). The X-ray diffraction diagram of FIG. 6(b) shows that the salicylic acid is combined with the yttrium hydroxide compound (YHC).

Example 7 Preparation of Composite (YHC-KA) of Kojic Acid Combined with Rare-Earth Hydroxide Compound The powder of the yttrium hydroxide compound (YHC) obtained in the Example 1 was added to a mixed solution of ethanol and distilled water (v/v=1:1) containing kojic acid and sodium hydroxide dissolved at an equivalent weight ratio of 1:1 and allowed to undergo a reaction at least 24 hours. The precipitate thus obtained was collected through centrifugal separation, washed and dried into a powder type composite (YHC-KA) of kojic acid combined with the yttrium hydroxide compound (YHC). The X-ray diffraction diagram of FIG. 6(c) shows that the kojic acid is combined with the yttrium hydroxide compound (YHC).

Example 8 Preparation of Composite (YHC-ALA) of Alpha-Lipoic Acid Combined with Rare-Earth Hydroxide Compound The powder of the yttrium hydroxide compound (YHC) obtained in the Example 1 was added to a solution containing alpha-lipoic acid and sodium hydroxide dissolved at an equivalent weight ratio of 1:1 and allowed to undergo a reaction under low pressure for at least 24 hours. The precipitate thus obtained was collected through centrifugal separation, washed and dried into a powder type composite (YHC-ALA) of alpha-lipoic acid combined with the yttrium hydroxide compound (YHC). The X-ray diffraction diagram of FIG. 6(d) shows that the alpha-lipoic acid is combined with the yttrium hydroxide compound (YHC).

Example 9 Preparation of Composite (YHC-EA) of Ellagic Acid Combined with Rare-Earth Hydroxide Compound The powder of the yttrium hydroxide compound (YHC) obtained in the Example 1 was added to a solution containing ellagic acid and sodium hydroxide dissolved at an equivalent weight ratio of 1:4 and allowed to undergo a reaction at 50° C. or above under low pressure for at least 24 hours. The precipitate thus obtained was collected through centrifugal separation, washed and dried into a powder type composite (YHC-EA) of ellagic acid combined with the yttrium hydroxide compound (YHC). The X-ray diffraction diagram of FIG. 6(e) shows that the ellagic acid is combined with the yttrium hydroxide compound (YHC).

Example 10 Preparation of Composite (YHC-RSV) of Resveratrol Combined with Rare-Earth Hydroxide Compound The powder of the yttrium hydroxide compound (YHC) obtained in the Example 1 was added to a mixed solution of ethanol and distilled water (v/v=1:1) containing resveratrol and sodium hydroxide dissolved at an equivalent weight ratio of 1:1 and allowed to undergo a reaction at 50° C. or above under low pressure for at least 24 hours. The precipitate thus obtained was collected through centrifugal separation, washed with distilled water and then dried into a powder type composite YHC-RSV) of resveratrol combined with the yttrium hydroxide compound (YHC). The X-ray diffraction diagram of FIG. 6(f) shows that the resveratrol is combined with the yttrium hydroxide compound (YHC).

Examples 11, 12 and 13 Preparation of Composite (YHC-UFA) of Unsaturated Fatty Acid Combined with Rare-Earth Hydroxide Compound The powder of the yttrium hydroxide compound (YHC) obtained in the Example 1 was added to a solution containing an unsaturated fatty acid (e.g., docosahexaenoic acid (DHA), eicosapentaenoic acid (EPA) or linoleic acid (LA)) and sodium hydroxide dissolved at an equivalent weight ratio of 1:1 and allowed to undergo a reaction at 50° C. or above for at least 24 hours. The precipitate thus obtained was collected through centrifugal separation, washed and dried into a powder type composite YHC-UFA) of the unsaturated fatty acid combined with the yttrium hydroxide compound (YHC). The X-ray diffraction diagrams of FIGS. 6(g), 6(h) and 6(i) show that the unsaturated fatty acids are combined with the yttrium hydroxide compound (YHC).

Example 14 Preparation of Composite (YHC-GLT) of Glutathione Combined with Rare-Earth Hydroxide Compound The powder of the yttrium hydroxide compound (YHC) obtained in the Example 1 was added to a solution containing glutathione and sodium hydroxide dissolved at an equivalent weight ratio of 1:2 and allowed to undergo a reaction at 50° C. or above under low pressure for at least 24 hours. The precipitate thus obtained was collected through centrifugal separation, washed and dried into a powder type composite YHC-GLT) of glutathione combined with the yttrium hydroxide compound (YHC). The X-ray diffraction diagram of FIG. 6(j) shows that the glutathione is combined with the yttrium hydroxide compound (YHC).

Experimental Example 1 Evaluation on Stability of Pure Vitamin C and YHC-Vc in Aqueous Solution An aqueous solution (a) containing 3.0 wt % of vitamin C and a dispersed solution (b) containing 10.0 wt % of the composite (YHC-Vc) prepared in the Example 2 (with a vitamin C content of about 30 wt % or greater per unit weight) were separately put in an airtight glass container and observed in regards to the change of color and pH at 50° C. for four weeks.

Figure 7:
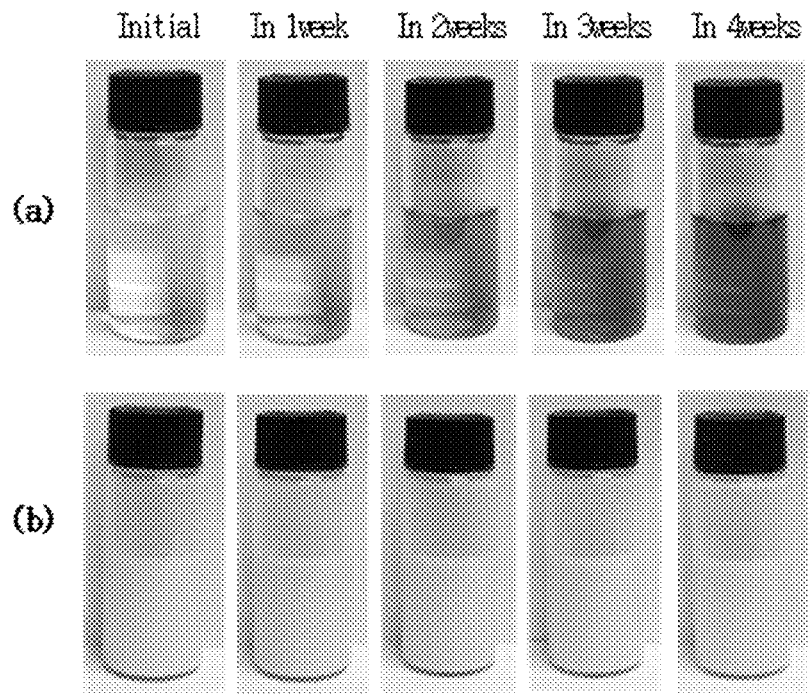
FIG. 7 shows the change of color in (a) a solution containing vitamin C; and (b) a dispersed solution containing a composite (YHC-Vc) of vitamin C combined with the yttrium hydroxide compound according to the present invention for four weeks while kept at 50° C. in an airtight container.

As shown in FIG. 7, the aqueous solution (a) containing 3.0 wt % of vitamin C had an abrupt change of color in the order from clear (colorless) to yellow, orange, and then red with an elapse of time, while the dispersed solution (b) of the composite (YHC-Vc) containing vitamin C combined with the yttrium hydroxide compound had no significant change of color.

Further, as can be seen from the following Table 2, the solution of pure vitamin C was maintained in the strong acid condition (pH ~2) for 4 weeks, while the solution of the composite (VHC-Vc) was maintained in the neutral condition (pH ~7) at 50° C. for 4 weeks.

TABLE 2

Change of pH for 4 weeks at 50° C. in Airtight Container

|  | Initial | In 1 week | In 2 weeks | In 3 weeks | In 4 weeks |
|---|---|---|---|---|---|
| (a) | 2.74 | 2.62 | 2.62 | 2.63 | 2.52 |
| (b) | 7.46 | 7.15 | 6.86 | 6.90 | 6.58 |

(a) Solution containing 3.0 wt % of vitamin C
(b) Dispersed solution containing 10.0 wt % of YHC-Vc prepared in Example 2

Figure 8:
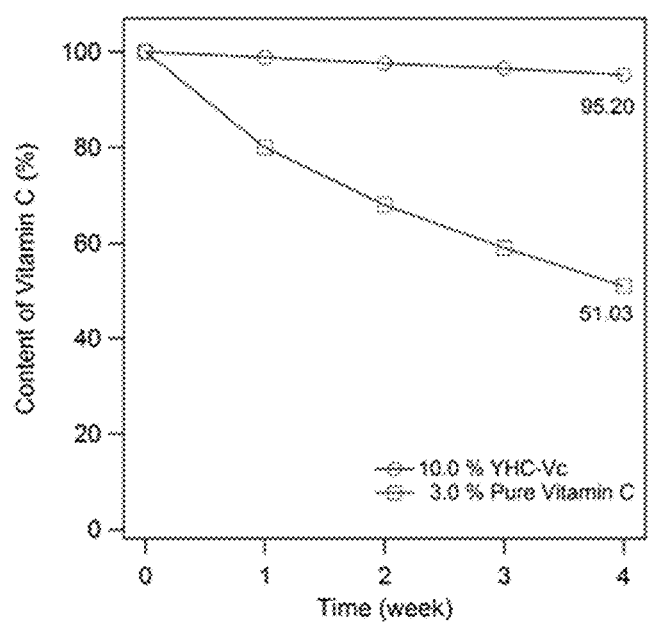
FIG. 8 shows the change of vitamin C content in (a) a solution containing vitamin C; and (b) a dispersed solution containing a composite (YHC-Vc) of vitamin C combined with the yttrium hydroxide compound according to the present invention for four weeks while kept at 50° C. in an airtight container.

FIG. 8 shows the change of the vitamin C content for the solution (a) of vitamin C and the dispersed solution (b) of the composite (YHC-Vc) of vitamin C combined with the yttrium hydroxide compound according to the present invention at 50° C. in an airtight container for four weeks. In four weeks, the remaining amount of vitamin C was about 51% in the solution (a) containing vitamin C and about 95% or greater in the dispersed solution (b) of the YHC-Vc composite. This explicitly shows that the vitamin C inserted into or adsorbed on surface of the yttrium hydroxide compound (YHC) was effectively stabilized.

Experimental Example 2 Evaluation on Stability of YHC-Vc Depending on pH

The composite (YHC-Vc) of vitamin C combined with the yttrium hydroxide compound as prepared in the Example 2 (containing at least about 30 wt % of vitamin C per unit weight) was added to a solution varied in pH (pH=3, 4, or 5) and dispersed to 10.0 wt %. The resultant solution was put in an airtight glass container and observed in regards to the change of color and pH value at 50° C. for four weeks.

Figure 9:
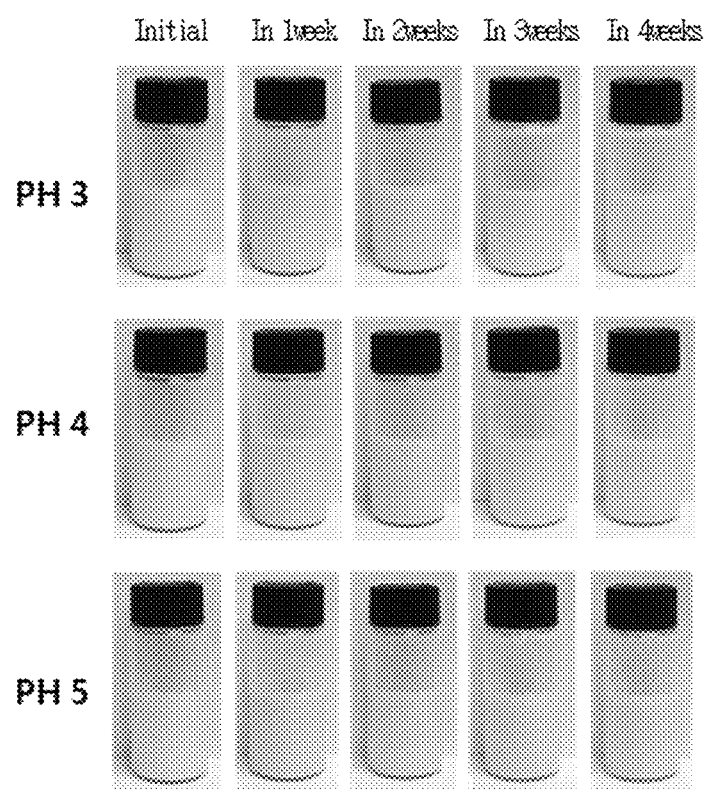
FIG. 9 shows the change of color in dispersed solutions containing a composite (YHC-Vc) of vitamin C combined with the yttrium hydroxide compound according to the present invention at different initial pH values of 3, 4, and 5 for four weeks while kept at 50° C. in an airtight container.

As shown in FIG. 9, there was no change of color in all the dispersed solutions of YHC-Vc for four weeks independent of the initial pH value.

In this regard, as presented in the following Table 3, the pH value was maintained for four weeks.

TABLE 3

Change of pH for 4 Weeks at 50° C. in Airtight Container

|  | Initial | In 1 week | In 2 weeks | In 3 weeks | In 4 weeks |
|---|---|---|---|---|---|
| pH 3 | 7.48 | 7.08 | 6.82 | 6.83 | 6.54 |
| pH 4 | 7.51 | 7.16 | 6.86 | 6.90 | 6.57 |
| pH 5 | 7.57 | 7.13 | 6.87 | 6.90 | 6.58 |

Figure 10:
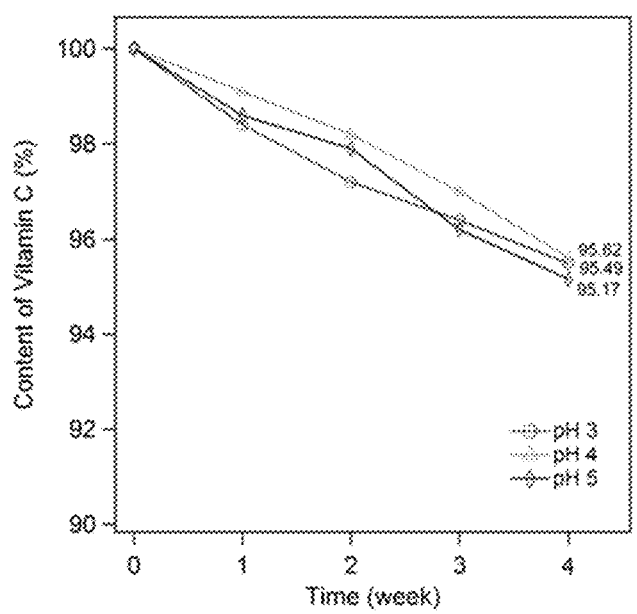
FIG. 10 shows the change of vitamin C content in dispersed solutions containing a composite (YHC-Vc) of vitamin C combined with the yttrium hydroxide compound according to the present invention at different initial pH values of 3, 4, and 5 for four weeks while kept at 50° C. in an airtight container.

FIG. 10 is a graph showing the change of the vitamin C content for the dispersed solution of the composite (YHC-Vc) containing vitamin C combined with the yttrium hydroxide compound according to the present invention in the pH 3, 4, or 5 conditions at 50° C. in an airtight container for four weeks. It is shown that at least about 95% of vitamin C was preserved in all the pH solutions at 50° C. in four weeks.

Experimental Example 3 Evaluation on Stability of Various Composites of YHC-Bioactive Compound Each solution containing 10 wt % of the composite containing a bio-active material combined with the yttrium hydroxide compound as dispersed in distilled water was put in an airtight glass container and observed in regards to the change of content at 50° C. from the initial stage to 4 weeks. More specifically, an evaluation on the stability at 50° C. in an airtight container for four weeks was performed for the composites of the Examples 5 to 12, namely, vitamin A composite (YHC-Ya), salicylic acid composite (YHC-SA), kojic acid composite (YHC-KA), alpha-lipoic acid composite (YHC-ALA), ellagic acid composite (YHC-EA), resveratrol composite (YHC-RSV), docosahexaenoic acid composite (YHC-DHA), eicosapentaenoic acid composite (YHC-EPA), linoleic acid composite (YHC-LA), and glutathione composite (YHC-GLT). The evaluation results are presented in the following Table 4.

TABLE 4

Change of Bio-active material Content in Composite of Bio-active material combined with Yttrium Hydroxide Compound

| Example | Composite | Initial | 1 week | 2 weeks | 3 weeks | 4 weeks |
|---|---|---|---|---|---|---|
| 5 | YHC-Va | 100.0% | 98.6% | 97.2% | 96.0% | 95.1% |
| 6 | YHC-SA | 100.0% | 99.5% | 99.8% | 99.5% | 99.6% |
| 7 | YHC-KA | 100.0% | 99.1% | 98.7% | 98.8% | 98.5% |
| 8 | YHC-ALA | 100.0% | 99.2% | 98.5% | 98.0% | 97.7% |
| 9 | YHC-EA | 100.0% | 99.2% | 98.6% | 97.7% | 97.2% |
| 10 | YHC-RSV | 100.0% | 98.4% | 97.5% | 96.1% | 94.9% |
| 11 | YHC-DHA | 100.0% | 99.7% | 99.4% | 99.6% | 99.5% |
| 12 | YHC-EPA | 100.0% | 99.8% | 99.4% | 99.7% | 99.6% |
| 13 | YHC-LA | 100.0% | 99.8% | 99.9% | 99.7% | 99.8% |
| 14 | YHC-GLT | 100.0% | 99.2% | 98.8% | 98.2% | 97.3% |

As can be seen from the results of Table 4, the dispersed solution of the bio-active material combined with the yttrium hydroxide compound had at least 95% of the bio-active material content stably preserved at high temperature of 50° C. for 4 weeks.

These results support that a variety of bio-active materials can be effectively stabilized through the formation of a composite with a rare-earth hydroxide compound.

The above-described present invention is not limited to the foregoing embodiments of the invention, and obviously many modifications and variations are possible without departing from the principles and the substantial scope of the present invention. The scope of the claims of the present invention includes such modifications and variations belonging to the principles of the present invention.

What is claimed is:

1. A composite containing a bio-active material combined with a rare-earth hydroxide compound, wherein the composite is represented by the following chemical formula 1:

$$[RE(OH)_{3-x} \cdot yH_2O] \cdot [A^n]_{x/n} \cdot [B]_z \quad \text{[Chemical Formula 1]}$$

wherein RE is at least one or more rare-earth element selected from the group consisting of yttrium (Y), gadolinium (Gd) and europium (Eu); A is an anion selected from the group consisting of $F^-$, $Cl^-$, $ClO_3^-$, $ClO_4^-$, $Br^-$, $BrO_3^-$, $IO_3^-$, $IO_4^-$, $I_3^-$, $OH^-$, $CO_3^{2-}$, $HCO_3^-$, $NO_3^-$, $SO_4^{2-}$, $PO_4^{3-}$, $HPO_4^{2-}$, and $H_2PO_4^-$; y is greater than zero, that is, $0<y$; n is the charge number of the anion; x is greater than 0 and less than 3, that is, $0<x<3$; B is a bio-active material; and z is greater than zero, that is, $0<z$;

wherein the rare-earth hydroxide compound has a layered structure; and wherein the bio-active material is at least one or more selected from the group consisting of vitamin C, vitamin A, salicylic acid, kojic acid, alpha-lipoic acid, ellagic acid, resveratrol, caffeine, docosahexaenoic acid, eicosapentaenoic acid, linoleic acid and glutathione.

2. The composite as claimed in claim 1, wherein the bio-active material comprises Vitamin C; and the rare-earth hydroxide compound comprises yttrium hydroxide.

3. The composite as claimed in claim 1, wherein the bio-active material comprises Vitamin C; and the rare-earth hydroxide compound comprises gadolinium/europium hydroxide.

4. The composite as claimed in claim 1, wherein the bio-active material comprises Vitamin A; and the rare-earth hydroxide compound comprises yttrium hydroxide.

5. The composite as claimed in claim 1, wherein the bio-active material comprises salicylic acid; and the rare-earth hydroxide compound comprises yttrium hydroxide.

6. The composite as claimed in claim 1, wherein the bio-active material comprises kojic acid; and the rare-earth hydroxide compound comprises yttrium hydroxide.

7. The composite as claimed in claim 1, wherein the bio-active material comprises alpha-lipoic acid; and the rare-earth hydroxide compound comprises yttrium hydroxide.

8. The composite as claimed in claim 1, wherein the bio-active material comprises ellagic acid; and the rare-earth hydroxide compound comprises yttrium hydroxide.

9. The composite as claimed in claim 1, wherein the bio-active material comprises resveratrol; and the rare-earth hydroxide compound comprises yttrium hydroxide.

10. The composite as claimed in claim 1, wherein the bio-active material comprises docosahexaenoic acid; and the rare-earth hydroxide compound comprises yttrium hydroxide.

11. The composite as claimed in claim 1, wherein the bio-active material comprises eicosapentaenoic acid; and the rare-earth hydroxide compound comprises yttrium hydroxide.

12. The composite as claimed in claim 1, wherein the bio-active material comprises linoleic acid; and the rare-earth hydroxide compound comprises yttrium hydroxide.

13. The composite as claimed in claim 1, wherein the bio-active material comprises glutathione; and the rare-earth hydroxide compound comprises yttrium hydroxide.

14. The composite as claimed in claim 1, wherein RE is Y.

* * * * *